United States Patent [19]

Liudzius et al.

[11] Patent Number: 4,872,052
[45] Date of Patent: Oct. 3, 1989

[54] SEMICONDUCTOR DEVICE INSPECTION SYSTEM

[75] Inventors: Valerie A. Liudzius, Simi Valley; Ralph M. Weisner, Canoga Park, both of Calif.; Takashi Kamiharako; Iwami Uramoto, both of Tokyo, Japan

[73] Assignees: View Engineering, Inc., Simi Valley, Calif.; Kaijo Denki Co., Ltd., Tokyo, Japan; a part interest

[21] Appl. No.: 128,329

[22] Filed: Dec. 3, 1987

[30] Foreign Application Priority Data

Dec. 3, 1986 [JP] Japan .................. 61-286881
Dec. 3, 1986 [JP] Japan .................. 61-286882
Dec. 3, 1986 [JP] Japan .................. 61-286883

[51] Int. Cl.⁴ ............................... H04N 7/18
[52] U.S. Cl. ..................... 358/106; 358/107; 350/511; 350/515; 356/237; 356/394
[58] Field of Search ............... 358/106, 101, 107, 88; 350/511, 513, 514, 515, 520–522; 356/237, 394; 382/8

[56] References Cited

U.S. PATENT DOCUMENTS

| | | | |
|---|---|---|---|
| 4,343,553 | 8/1982 | Nakagawa et al. | 368/101 |
| 4,491,868 | 1/1985 | Berridge et al. | 358/106 |
| 4,538,909 | 9/1985 | Bible et al. | 356/237 |
| 4,589,140 | 3/1986 | Bishop et al. | 358/106 |
| 4,628,531 | 12/1986 | Okamoto et al. | 382/8 |
| 4,651,200 | 3/1987 | Ledly | 350/520 |
| 4,659,220 | 4/1987 | Bronte et al. | 356/237 |
| 4,671,446 | 6/1987 | Sherman | 250/225 |
| 4,700,225 | 10/1987 | Hara et al. | 358/106 |
| 4,717,246 | 1/1988 | Fehr et al. | 350/520 |

FOREIGN PATENT DOCUMENTS

| | | |
|---|---|---|
| 59-139638 | 8/1984 | Japan . |
| 59-139639 | 8/1984 | Japan . |
| 59-144140 | 8/1984 | Japan . |
| 61-716944 | 4/1986 | Japan . |
| 61-144837 | 7/1986 | Japan . |
| 61-148828 | 7/1986 | Japan . |

Primary Examiner—John K. Peng
Attorney, Agent, or Firm—Merchant, Gould, Smith, Edell, Welter & Schmidt

[57] ABSTRACT

A semiconductor device inspection system capable of objectively accomplishing visual image inspection of a semiconductor device and minimizing error in the inspection, to thereby effectively carry out the inspection with high accuracy and at high speed. The system includes a low magnification image pickup mechanism which consists of a plurality of low magnification image pickup units each carrying out low magnification image pickup of a semiconductor device to generate an image signal. The system also includes a signal processing system for processing the image signal to judge the correctness of the semiconductor device. In the image pickup units, their light receptors are each arranged in parallel to an inspected surface of the semiconductor device and their central axes intersect together on the inspected surface. The system may also include a high magnification image pickup unit consisting of a high magnification image pickup mechanism and a light-permeable element retractably positioned between the unit and a semiconductor device to be inspected.

18 Claims, 9 Drawing Sheets

SEMICONDUCTOR DEVICE INSPECTION SYSTEM

BACKGROUND OF THE INVENTION

1. Field of the Invention

This invention relates to a semiconductor device inspection system for inspection of a semiconductor device, and more particularly to a system for inspecting the visual image of a semiconductor device by image pickup during manufacturing.

2. Description of the Prior Art

Conventionally, so-called wire bonding formed by connecting an IC chip and a lead on a base plate or substrate of a semiconductor device by means of a wire has been inspected manually and visually. Wire bonding items inspected included, for example, lack of a wire, breaking of a wire, mis-bonding of a wire (bonding of a wire to an incorrect position), the degree of wire projection, wire curling (unnecessary curling of a wire), raising of a bonding section, the position of bonding with respect to a pad or a lead, the dimensions and the shape of a ball or a stitch, and the like. Typically, the items from "lack of a wire" to "raising of a bonding section" are visually inspected by means of a microscope of low magnification having a wide visual field covering an IC chip and a bonding section formed around the chip.

The conventional inspection described above permits a three-dimensional configuration of a wire to be perceived by means of a binocular microscope; however, it has the disadvantage of requiring much time for inspection. Thus inspection efficiency is lowered because it is necessary to carry out the inspection on many items and on many bonding sections. Also, judgment of the correctness of the bonding is conventionally made on the basis of perception and/or the experience of an inspector, resulting in the inspection varying depending on the inspector. Further, visual inspection using a microscope is carried out in a direction from one side of a semiconductor device to the other side thereof. This leads to error in the inspection of deflection of a wire or the like because a distorted microscope image appears due to the distance from the microscope to the semiconductor device, resulting in deterioration of the accuracy of the inspection.

Recently, an image pickup device has been proposed which is adapted to use a lens of a high magnification to carry out plane image pickup substantially in parallel to a substrate for visual image inspection of a bonding section on a semiconductor device. However, in the image pickup device, it is necessary to adjust the focus of the device by varying the focal distance of the device or carrying out relative movement between the device and the substrate when a pad and a lead are not on the same image pickup plane.

Also, the conventional image pickup device unfortunately has a small focal depth because of using a lens of a high magnification, so that focus adjustment of the device is highly troublesome.

Further, an attempt has been made to use the image pickup device for inspecting the amount of deformation of a wire in the direction of its height. For this purpose, a camera of the device was vertically moved to focus the camera on each vertical position of the wire. However, it is required to horizontally move the camera with respect to each pad and lead because the lens has a high magnification and a small visual field, resulting in substantial deterioration of inspection efficiency.

Further, it takes much time to transfer the image pickup device for image pickup, resulting in a lowering in inspection efficiency and speed Accordingly, it would be highly desirable to develop a system for inspection of a semiconductor device which is capable of determining the correctness of the inspection, objectively accomplishing the inspection and minimizing or substantially eliminating errors in the inspection, and minimizing errors in the inspection due to a distorted image which appears due to distance, to thereby inspect the visual image of a semiconductor device with high accuracy and efficiency and at high speed.

SUMMARY OF THE INVENTION

Generally speaking, in accordance with the present invention, a semiconductor device inspection system in provided which is adapted to carry out visual image inspection of a semiconductor device subjected to wire bonding and supported on a base. The semiconductor device inspection system includes at least one image pickup mechanism comprising a plurality of image pickup units. The image pickup units each carry out plane image pickup of the semiconductor device to generate an image signal and include a lens system having at least one lens and a light receptor for receiving thereon an image formed by the lens system. The inspection system also includes an optical-electrical signal converter means, which is connected to the image pickup units to convert each of the image signals into an electrical signal. The optical-electrical signal converter is then connected to an operation circuit which is constructed to digitize the electrical signal. The operation circuit carries out digitizing of electrical signals derived from at least two of the image pickup units and converted by the converter and synthetically operates the digitized electrical signals to obtain data on a three-dimensional position of an inspected section of the semiconductor device. The inspection system further includes a memory circuit for storing digitized standard data on an inspection item therein and an image processing unit connected to the operation circuit to compare an input data signal obtained by digitizing the electrical signal with a standard data signal based on the digitized standard data to judge normality of the input data signal. The image pickup units are arranged in a manner such that the light receptor of each of the image pickup units is arranged in parallel to an inspected surface of the semiconductor device and central axes of the image pickup units each defined by connecting a center of the light receptor and a center of the lens system together intersect one another on the inspection surface of the semiconductor device.

In accordance with the present invention, there is also provided a semiconductor device inspection system which is adapted to carry out visual image inspection of a semiconductor device subjected to wire bonding and supported on a base. The inspection system includes a loading mechanism for receiving therein a semiconductor device which has been subjected to wire bonding. The semiconductor device is then transferred from the loading mechanism through an inspection stage and then discharged from the transfer mechanism by means of an unloading mechanism upon completion of the inspection. The inspection system also includes an image pickup means for carrying out image pickup of the semiconductor device on the inspection stage to generate an image signal, a memory circuit for storing standard data therein, and an image processing unit connected between the image pickup means and the memory circuit to carry out digital processing of the image signal and compare the digitized image signal with the standard data stored in the memory circuit to judge the correctness of the wire bonding and generate a judgment signal. Further, the inspection system includes a marking mechanism for carrying out marking indicative of the correctness of the semiconductor device depending on the judgment signal from the image processing unit.

Further, in accordance with the present invention, a semiconductor device inspection system in provided which is adapted to carry out high magnification image pickup of a semiconductor device. The inspection system includes a base for holding a semiconductor device thereon and an image pickup mechanism for carrying out high magnification plane image pickup of the semiconductor device to inspect the visual image of the semiconductor device at high magnification. The image pickup mechanism comprises an image pickup unit and a light-permeable element having a refractive index different from that of air. The light-permeable element is arranged in a manner to be retractably interposed between the image pickup unit and the semiconductor device.

Accordingly, it is an object of the present invention to provide a system for inspection of a semiconductor device which is capable of readily and efficiently inspecting the visual image of a semiconductor device by plane image pickup at high speed and with high accuracy.

It is another object of the present invention to provide a semiconductor device inspection system which is capable of carrying out visual image inspection of a semiconductor device by plane image pickup without varying to focal distance of an image pickup unit.

It is a further object of the present invention to provide a semiconductor device inspection system which is capable of precisely accomplishing a visual image inspection of a semiconductor device at high speed by subjecting a plurality of sites to be inspected which are not on the same plane to plane image pickup.

It is still another object of the present invention to provide a semiconductor device inspection system which is capable of improving inspection efficiency.

It is yet another object of the present invention to provide a semiconductor device inspection system which is capable of determining the correctness of the inspection, objectively accomplishing the inspection, and minimizing or substantially eliminating error in the inspection.

It is still a further object of the present invention to provide a semiconductor device inspection system which is capable of minimizing errors in the inspection due to a distorted image which appears due to distance.

It is yet a further object of the present invention to provide a semiconductor device inspection system which is capable of accomplishing the above-noted objects with a significantly simplified structure.

Still other objects and advantages of the invention will in part be obvious and will in part be apparent from the specification.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings in which like reference numerals designate like or corresponding parts throughout; wherein.

DETAILED DESCRIPTION OF THE INVENTION

Now, a semiconductor device inspection system according to the present invention will be described hereinafter with reference to the accompanying drawings.

Figure 1:
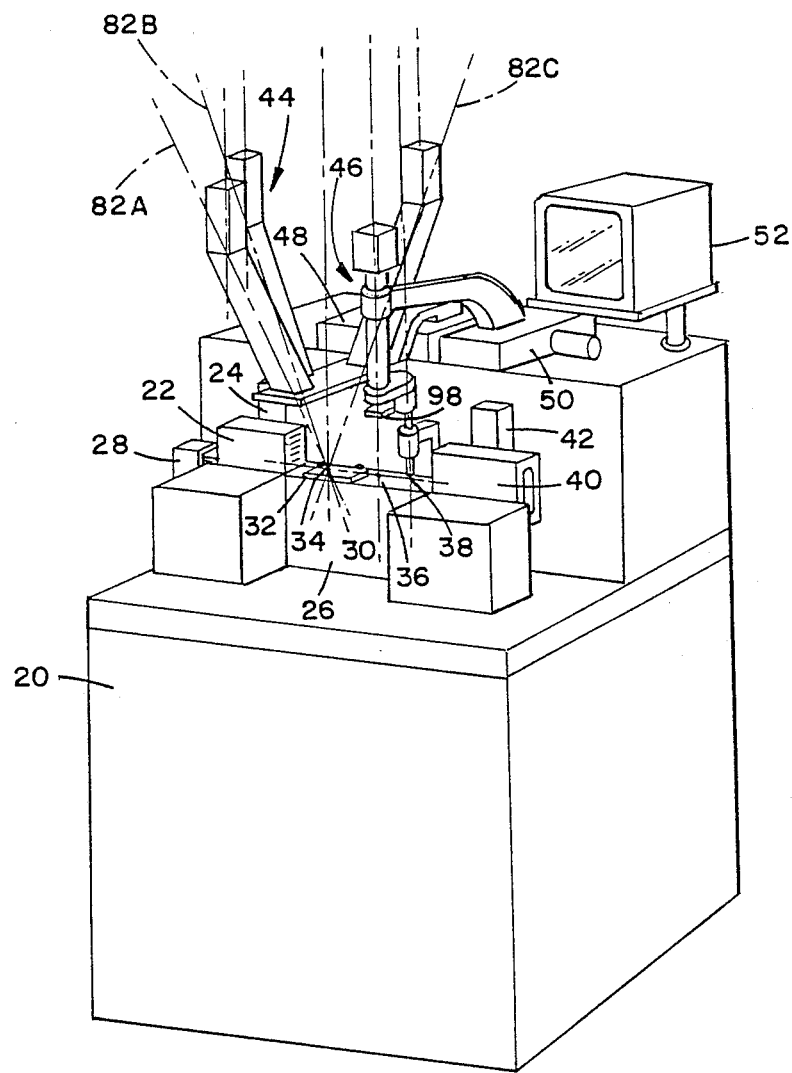
FIG. 1 is a perspective view showing an embodiment of a semiconductor device inspection system according to the present invention.

FIG. 1 shows an embodiment of a semiconductor device inspection system according to the present invention. A semiconductor device inspection system of the illustrated embodiment includes a table or base 20. On the base 20 are arranged a feed magazine 22 for receiving therein semiconductor devices such as lead frames which have been subjected to a wire bonding treatment, an elevator 24 for vertically moving the feed magazine 22, an inspection station or stage 26 on which visual image inspection of a semiconductor device is carried out, a push-out mechanism 28 for supplying semiconductor devices received in the magazine 22 to the inspection stage 26 one by one, a transfer mechanism 30 for intermittently transferring a semiconductor device 32 on the inspection stage 26 to a low magnification inspection point or position 34, a high magnification inspection point or position 36 and a marking station 38 respectively, a storage magazine 40 for receiving therein semiconductor devices which have been inspected and marked, and an elevator 42 for vertically moving the storage magazine 40. The elevator 24 may be constructed in such a manner as disclosed in, for example, Japanese Utility Model Application No. 109/1985, Japanese Utility Model Application No. 1346/1985 or Japanese Utility Model Application No. 1926/1985. The push-out mechanism 28 may be constructed in such a manner as disclosed in, for example, Japanese Patent Application No. 152633/1986. A plurality of the transfer mechanisms 30 may be used as one set for concurrently transferring a plurality of semiconductor devices. Alternatively, plural sets of the transfer mechanisms may be arranged to independently or synchronously transfer semiconductor devices.

The embodiment shown in FIG. 1 further includes a low magnification image pickup mechanism 44. Also, it may include a high magnification image pickup mechanism 46. Both image pickup mechanisms 44 and 46 are may be arranged on X-Y tables 45 and 50, respectively. The low and high magnification image pickup mechanisms 44 and 46 are positioned to carry out image pickup of predetermined sections of a surface of the semiconductor device 32 at the low and high magnification inspection positions 34 and 36, respectively. The image pickup mechanisms 44 and 46 are connected to a visual monitor device 52 for displaying images picked up thereby.

The semiconductor device inspection system of the illustrated embodiment further includes a marking mechanism 54 which puts, at the marking station 38, a failure mark indicative of a "nonconforming article" on a semiconductor device which inspection has found to be defective.

Figure 2:
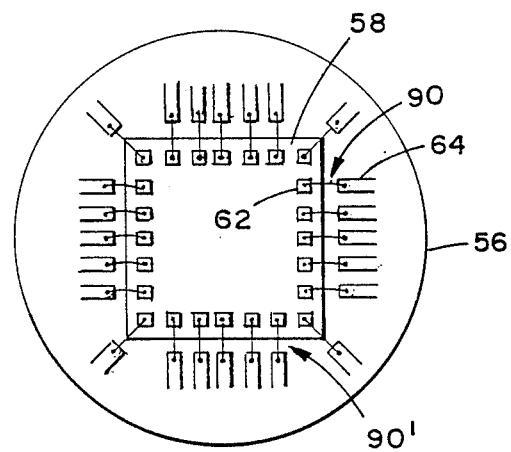
FIG. 2 is a schematic view showing a visual field obtained by a low magnification image pickup mechanism incorporated in the embodiment shown in FIG. 1.

The low magnification image pickup mechanism 44 may be constructed to have a visual field as indicated at reference numeral 56 in FIG. 2. More particularly, the visual field 56 may be determined to permit whole bonding formed around one IC chip 58 of a semiconductor device to be observed, so that the mechanism 44 may be adapted to typically inspect, for example, misregistration of the IC chip 58 and the configuration and dimensions of a wire loop.

When the IC chip 58 has a large-size like a VLSI, it may be divided into a plurality of inspected sections, which are then observed in order by the low magnification mechanism 44 successively moved by means of the X-Y table 48.

Figure 3:
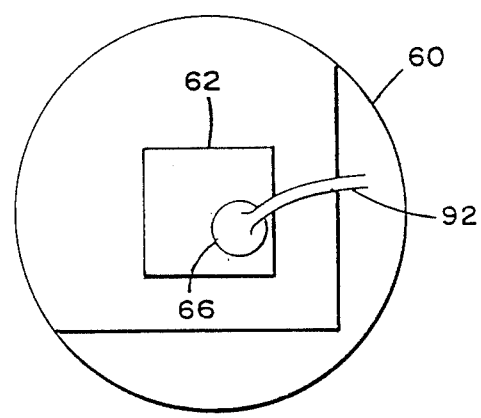
FIG. 3 is a schematic view showing a visual field obtained by a high magnification image pickup mechanism incorporated in the embodiment shown in FIG. 1.
Figure 7:
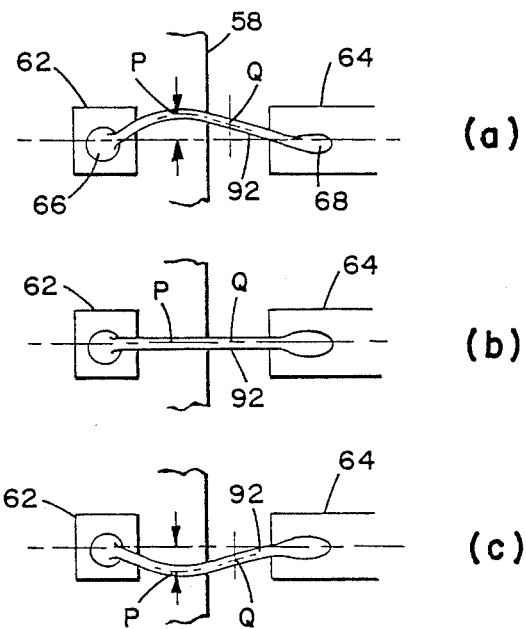
FIGS. 7(a), (b) and (c) are schematic views showing images of a certain bonding section picked up by three different low magnification image pickup units, respectively.
Figure 8:
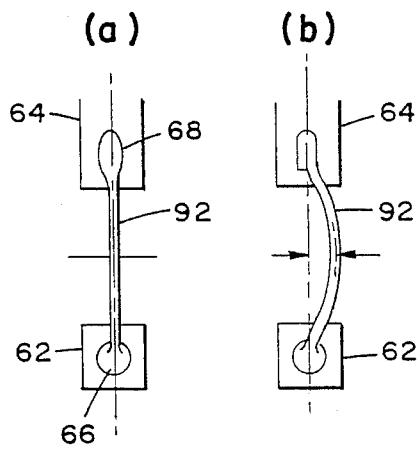
FIGS. 8(a) and (b) are schematic views showing images of another bonding section picked up by two different low magnification image pickup units, respectively.

The high magnification image pickup mechanism 4 may be constructed to have a visual field as indicated at reference numeral 60 in FIG. 3. It may be determined to permit bonding around one pad 62 or lead 64 or the IC chip 58 to be observed, so that the mechanism 46 may be adapted to typically inspect, for example, the position, the configuration and dimensions of each ball 66 and stitch 68 (FIGS. 7 and 8). The visual field 60 is moved over every pad 62 or lead 64. However, the position of each pad 62 is previously detected based on the amount of misregistration of the IC chip 58 detected by the low magnification image pickup mechanism 44 and stored in a memory circuit. Accordingly, it is not necessary that the high magnification image pickup mechanism 46 detect the position again at the time the visual field 60 moves. Thus, the visual field 60 may be rapidly moved toward the detected position.

Figure 4:
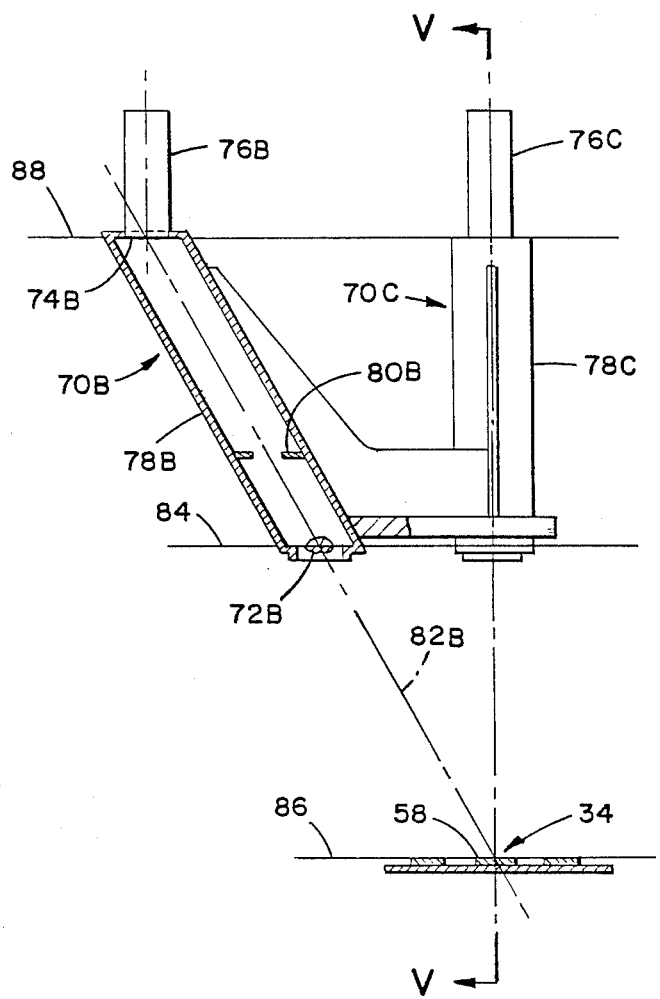
FIG. 4 is a front elevation view in section showing a low magnification image pickup mechanism, which is taken along a vertical plane parallel to the direction of transfer of a semiconductor device through a low magnification inspection position by the low magnification image pickup mechanism.
Figure 5:
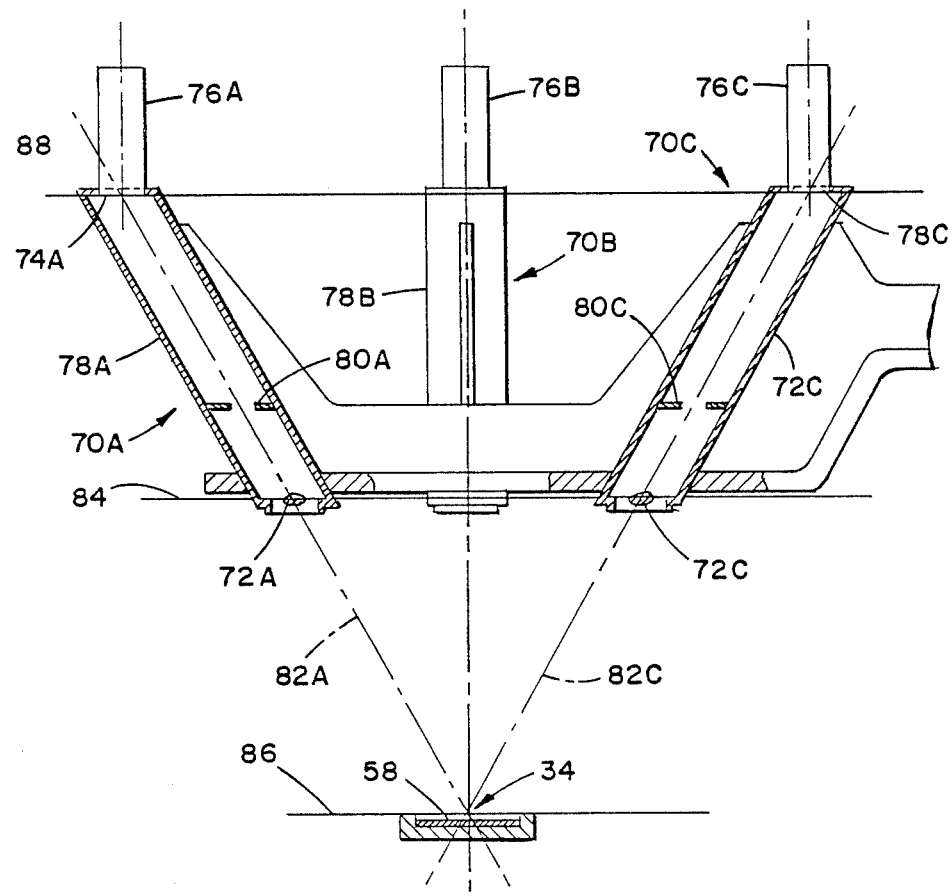
FIG. 5 is a sectional view taken along line V-V of FIG. 4.
Figure 6:
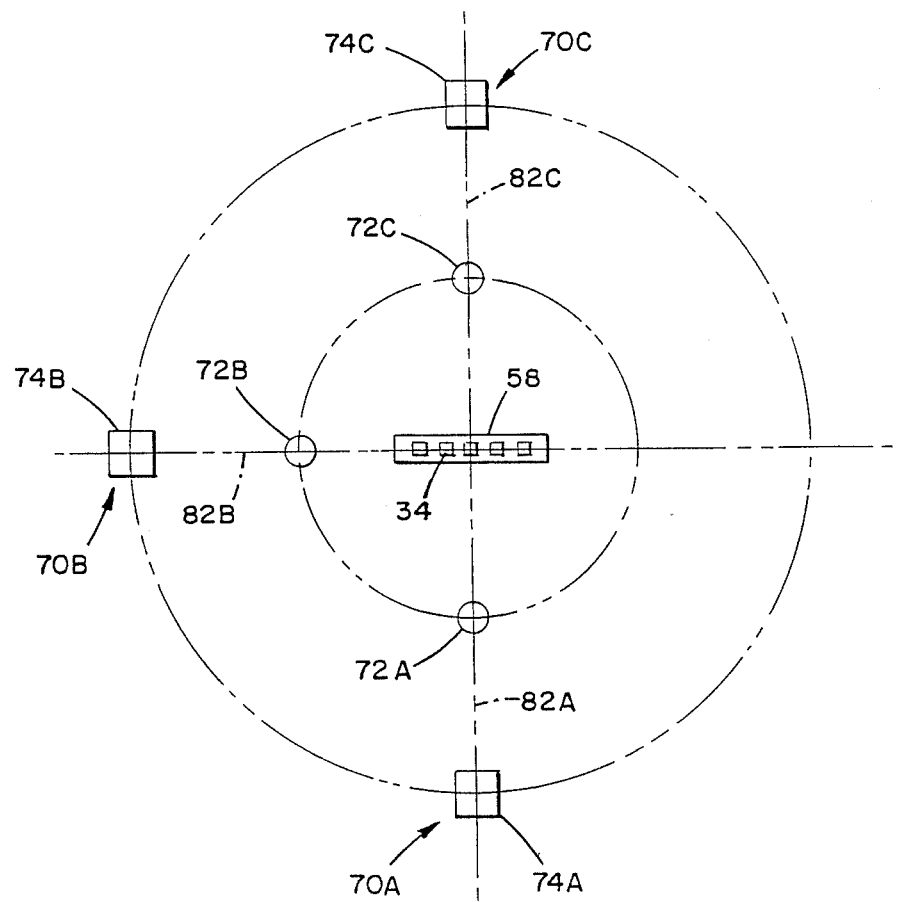
FIG. 6 is a plan view schematically showing arrangement of a low magnification image pickup mechanism.

The low magnification image pickup mechanism 44 may be constructed in such a manner as shown in FIGS. 4 to 6.

More particularly, the low magnification image pickup 44 includes low magnification image pickup units 70A, 70B and 70C which comprise a lens system 72A including at least one lens, a light receptor 74A including a vidicon, a solid image pickup element or the like, a lens barrel 78B and a diaphragm 80A; a lens system 72B, a light receptor 74B including a vidicon, a solid image pickup element or the like, a lens barrel 78B and a diaphragm 80B; and a lens system 72C, a light receptor 74C including a vidicon, a solid image pickup element or the like, a lens barrel 78C and a diaphragm 80C respectively. The low magnification image pickup units 70A, 70B and 70C are connected to optical-electrical signal converters 76A, 76B and 76C, respectively. Each central axis 82 obtained by connecting a center of each receptor 74 and a center of each lens system 72 is defined so as to be aligned with the low magnification inspection position or point 34 on the inspection stage 26. Also, the central axes 82A, 82B and 82C, as shown in FIG. 6, are so defined that the central axes 82A and 82C may be opposite to each other or spaced at an angle of 180 degrees from each other and the central axis 82B may be perpendicular to the central axes 82A and 82C, when they are viewed planely. Each of the lens systems 72A, 72B and 72C is arranged in a manner such that its lens plane 84, which is perpendicular to a main axis thereof, is parallel to a surface or plane 86 of the IC chip 58 which is to be inspected. Likewise, each of the light receptors 74A, 74B and 74C is arranged to cause its light receiving plane 88 to be parallel to the surface 86 of the IC chip 58. Thus, in the illustrated embodiment, the planes 84, 86 and 88 are parallel to one another.

The low magnification image pickup units 70A, 70B and 70C constructed and arranged in the manner described above cause an image of the IC chip 58 formed on each of the light receptors 74A, 74B and 74C to be focused on the whole visual field 56 shown in FIG. 2. Also, such construction and arrangement of the low magnification image pickup units causes the image to be formed in a proper shape, such as a rectangle, on the light receptors 74A, 74B and 74C without distortion due to the amount of distance from the lens systems 72A, 72B and 72C to the IC chip 58, i.e. due to the differences of distance from the predetermined lens to the different points of the IC ship 58, as if image pickup is carried out from right above.

Low magnification image pickup by the image pickup mechanism 44 is carried out in an oblique direction, so that when the surface 86 of the IC chip 58 has any irregularity, images of the chip obtained by the low magnification image pickup units, 70A, 70B and 70C are rendered differently in shape and dimensions from one another. A signal of an average position on each light receptor 74 which is obtained by digitizing image pickup signals of at least two of the image pickup units 70A, 70B and 70C is operated by an operation circuit for synthesis, so that a three-dimensional position of each inspected section on the IC chip 58 may be calculated to obtain a digital signal indicating dimensions and the shape of the section. Such an operation circuit may be arranged in a central processing unit (CPU) or a pattern recognition unit (PRU) described hereinafter.

When the three low magnification image pickup units 70A, 70B and 70C carry out image pickup of the IC chip 58 constructed as shown in FIG. 2, images of each portion of, for example, a bonding section 90 obtained by the units 70A, 70B and 70C are shown in FIGS. 7(a), 7(b) and 7(c), so long as it is properly formed. Then, two of the so-obtained images are scanned to obtain the digital amount of a plane position of each portion, which is then used for synthetic operation to obtain a three-dimensional position of a predetermined point on a wire 92, such as P, Q, or the like.

Further, when another bonding section, for example, a bonding section 90', is properly formed, the image pickup units 70A and 70C carry out image pickup of the section 90' as shown in FIG. 8(a) and the unit 70B carries out image pickup as shown in FIG. 8(b). The so-obtained two images are then scanned to digitize each position on the wire 92 for synthetic operation, resulting in the obtaining of a three-dimensional position of any point on the wire 92.

A digital input data signal of the actual article of IC chip 58 which has been obtained in the manner described above is then compared with a digital standard data signal previously stored in a memory circuit described hereinafter to inspect any failure in bonding of a wire on the IC chip 58 due to misregistration of the wire, lack of a wire, breaking of a wire, mis-bonding of the wire, improper height of the wire, curling of the wire or the like.

Low magnification inspection of the bonding may be carried out with respect to each wire. However, the low magnification image pickup mechanism 44 permits a plurality of wires in each of the blocks defined by dividing the IC chip 58 to be scanned as a group for concurrent inspection. This results in the inspection time being significantly shortened. Also, the low magnification image pickup mechanism 44 permits an acceptable limit to be indicated in a numerical form to minimize variations in inspection an properly focus on each visual field of an inspected surface. Further, it causes the image obtained to be substantially free of distortion due to the distance from the receptor 74 to the IC chip 58. Thus, it will be noted that the mechanism 44 accomplishes image pickup with high accuracy.

In the illustrated embodiment, the low magnification image pickup mechanism 44 includes one set of the image pickup units 70. However, it may be constructed to include two or more sets of such image pickup units. In this instance, the image pickup units of each set may be arranged to have their central axes defined in any direction. For example, in FIGS. 4 to 6, only the unit 70A may have a vertically extending central axis.

In the illustrated embodiment, a further low magnification image pickup unit may be vertically arranged right above the low magnification inspection position 343.

In the illustrated embodiment, the lens systems 72A, 72B and 72C each are arranged to have the lens plane 84 parallel to the surface 86 of the semiconductor device. However, the lens plane 84 of the lens system 72 may be perpendicular to the central axis 82. Such construction fails to cause the receptor 74 to be focused on the whole visual field 56; however, use of a lens having a large focal depth permits the receptor 74 to be satisfactorily focused on the whole visual field.

As described above, the semiconductor device inspection system of the illustrated embodiment may include the high magnification image pickup mechanism 46, which may be constructed to carry out observation of a pattern by such an image enlarged in a narrow visual field as indicated at reference numeral 60 in FIG. 3, for a subsequent comparison of misregistration between the ball 66 and the stitch 68 and the configuration and dimensions of the ball 66 with previously-stored standard data which is required for a visual image inspection.

It is not required that the inspection using the high magnification image pickup mechanism 46 be carried out with respect to all bonding sections. It may be carried out in the form of a sampling inspection. Also, in the high magnification inspection, it is not required to inspect the position of the pad 62 which has been already subjected to the low magnification inspection described above. This results in the high magnification inspection being accomplished in a short period of time, thus improving the efficiency of the whole inspection. Further, the high magnification image pickup mechanism 46 permits an acceptable limit to be indicated in a numerical form to minimize variations in the inspection, resulting in the inspection being accomplished with high accuracy.

The lens system used in the high magnification image pickup mechanism 46 is required to have high magnification, resulting in its focal depth being small. Accordingly, when there is any difference in the height between a surface of the pad 62 and that of the lead 64, it is necessary to separately focus the lens system on the pad and lead. For this reason, the high magnification image pickup mechanism 46 is arranged so as to be horizontally moved in X and Y directions and includes a high magnification image pickup device and a light-permeable element having a refractive index different from that of air.

Figure 9:
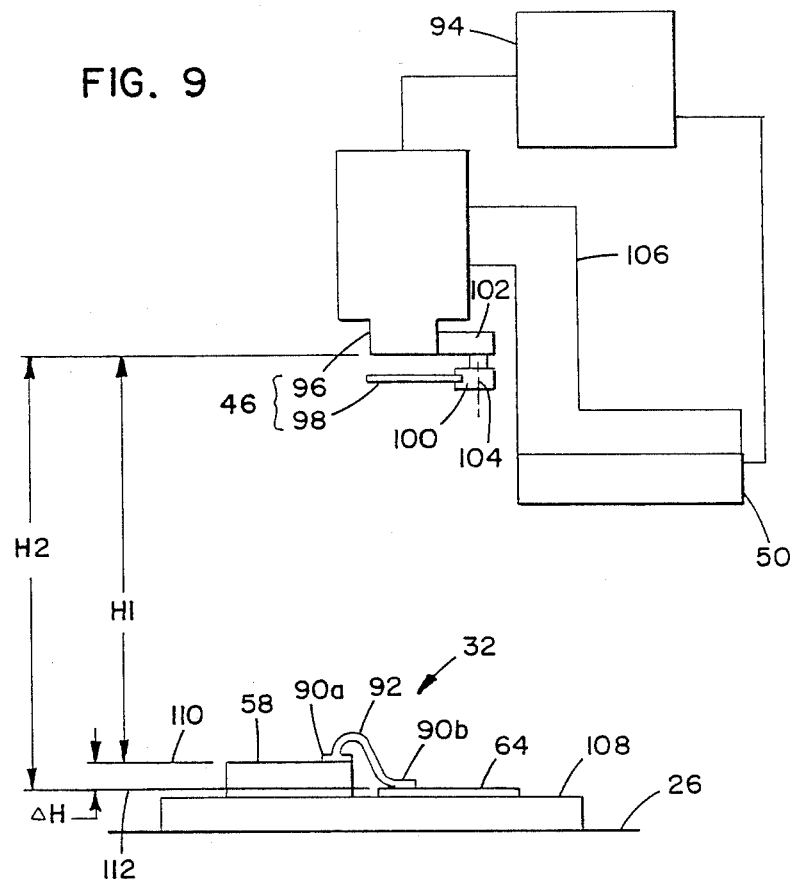
FIG. 9 is a schematic front elevation view showing another embodiment of a semiconductor device inspection system according to the present invention.

More particularly, the high magnification image pickup mechanism 46, as shown in FIG. 9, is so arranged that it may carry out high magnification image pickup of a plane of a semiconductor device 32 positioned at the high magnification inspection position 36 of the inspection station or stage 26 provided on the base or table 20. The high magnification image pickup takes places from right above. This results in the high magnification image pickup mechanism 46 generating an optical signal or image signal. The high magnification image pickup mechanism 46 may be connected through an optical-electrical signal converter (not shown) like the converter 76 to a signal processing means 94, described hereinafter, which is adapted to permit image signals generated from the mechanism 44 and 46 and fed thereto to be processed, so that a visual image inspection of the semiconductor device may be accomplished.

The high magnification image pickup mechanism 46 may comprise a high magnification image pickup device or unit 96 and a light-permeable element 98 having a refractive index different from that of air. The high magnification image pickup unit 96 may include a lens system comprising at least one lens and a light receptor element such as a vidicon, a solid image pickup element or the like, and is arranged so as to be upwardly spaced at a suitable distance from the inspection stage 26 and opposite thereto. The light-permeable element 98 is supported on a holder 100 in such a manner that it may be retractably positioned or interposed between the image pickup unit 96 and the semiconductor device 32. For this purpose, in the illustrated embodiment the holder 100 comprises an arm which is mounted at one end thereof on a mounting member 102 so as to be pivotable about a vertical axis 104 perpendicular to the inspection station 26 and the light-permeable element 98 comprises a flat glass member which has parallel surfaces and is mounted on the other end of the arm 100 so as to be parallel to the surface of the inspection stage 26.

The arm or holder 100 is rotated by a rotational actuation means (not shown) which is adapted to be driven according to a predetermined inspection procedure.

The inspection stage 26 and high magnification image pickup mechanism 46 are arranged so as to be moved relative to each other in a plane parallel to the surface of the inspection stage 26. In the illustrated embodiment, as described above, the image pickup mechanism 46 or unit 96 is disposed on the X-Y transfer mechanism or table 50, resulting in it being moved with respect to the inspection stage 26. More particularly, the mounting member 102 is connected to the high magnification image pickup unit 96, which is then connected through a support means 106 to the X-Y transfer mechanism or table 50. Alternatively, the mounting member 102 may be connected directly to the X-Y transfer mechanism or table 50. The X-Y table 50 is connected to the signal processing means 94 together with the X-Y table 48. Such construction permits the light-permeable element 98 and image pickup unit 96 to be moved together in an X- or Y-direction. Sites or sections on the semiconductor device to be inspected each are previously detected in the form of detection data in a previous step, and the X-Y transfer mechanism 50 is constructed to move the image pickup unit 96 to positions right above the inspected sites of the semiconductor device by means of the signal processing means 94 depending on the detection data.

In the high magnification image pickup mechanism shown in FIG. 9, the semiconductor device 32 put on the inspection stage 26 is shown as including a substrate 108 and an IC chip 58 and a lead 64 arranged on the substrate 108, and a wire 92 for connecting the IC chip 58 and lead 64 to each other by bonding. Also, the semiconductor device 32 is formed with a bonding section 90a between the IC chip 58 and the wire 92 and a bonding section 90b between the lead 64 and the wire 92. The bonding section 90a is positioned on a plane 110 downwardly spaced at a distance of H1 from the image pickup unit 96 and parallel to the surface of the inspection stage 26 and the bonding section 90b is formed on a plane 112 downwardly spaced at a distance H2 which is larger by H than the distance H1 from the image pickup unit 96 and parallel to the surface of the inspection stage 26. The high magnification image pickup unit 96 is previously vertically adjusted to permit the bonding section 90a between the IC chip 58 and the wire 92 and the bonding section 90b between the lead 64 and the wire 92 to be within the visual field 60 (FIG. 3) of the image pickup unit 96.

The optical system of the high magnification image pickup unit 96 has a focal distance which is so adjusted that image pickup of the bonding section 90a on the plane 110 may be carried out.

The light-permeable element or glass plate 98 used is adapted to satisfy the following equation (1):

$$H = (N - 1/N) T \quad (1)$$

wherein N and T are a refractive index and the thickness of the glass plate 98, respectively. For example, the thickness T of the glass plate 98 of which the refractive index N is 1.517 in the case that H is 127 μm is as follows:

$$T = H \times N/(N-1) \quad (2)$$

Accordingly, $$T = 127 \times 1.517/0.517$$

$$= 370$$

Thus, it will be noted that in this instance, the glass plate 98 to be used should have a thickness of 370 μm.

H is typically in a range between 0.3 mm and 0.5 mm and, in this case, the glass plate 98 having a refractive index of 1.517 is made to have a thickness in a range of from 0.88 mm to 1.47 mm. Accurate values of H and N are determined according to the above-described equation (2).

The bonding section 90a is prepared for high magnification image pickup and inspection thereof by moving the high magnification image pickup unit 96 to a position right above the bonding section 90a by means of the X-Y transfer mechanism or table 50 and pivotally moving the arm 100 to pivot the glass plate 98 in a direction apart from a lower portion of the image pickup unit 96. Then, the image pickup is carried out directly by means of the image pickup unit 96 without using the light-permeable element or glass plate 98. At this time, the unit 96 is automatically or previously focused on the bonding section 90a on the plane 112 to obtain a clear image of the bonding section.

Then, the bonding section 90b is prepared for high magnification image pickup and inspection thereof by moving the high magnification image pickup unit 96 to a position right above the bonding section 90b by means of the X-Y transfer mechanism or table 50 and pivotally moving the arm 100 about the vertical axis 104 to position the glass plate 98 right below the image pickup unit 96. Then, image pickup of the bonding section 90b is attained through the glass plate 98. The optical system of the whole high magnification image pickup mechanism 46 including the image pickup unit 96 and glass plate 98 has a focal distance different from that of the image pickup unit 96 due to the existence of the glass plate 98, so that it may be focused on the bonding section 90b to obtain an accurate and distinct image of the section 90b although the image pickup unit 96 itself is not varied in its focal distance.

Thus, it will be noted that the illustrated high magnification image pickup mechanism 46 permits image pickup and inspection of the bonding sections 90a and 90b varied in height to be accurately accomplished merely by pivoting the glass plate 98 to retractably position it between the image pickup unit 96 and the semiconductor device 32 without requiring any troublesome operation, such as relatively vertically moving the image pickup unit 96 and inspection stage 26 by a distance corresponding to the difference H for focusing the image pickup unit 96 on the bonding sections, varying the focal distance of the image pickup unit 96, or the like.

Figure 10:
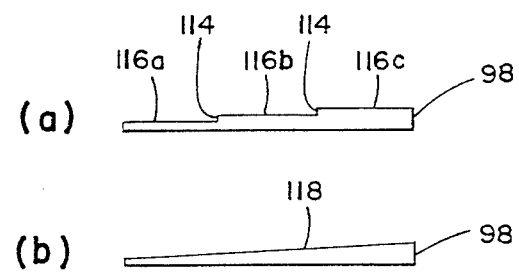
FIGS. 10(a) and (b) each are a side elevation view showing a modification of a light-permeable element.

In the illustrated embodiment, the holder or arm 100 may be constructed in such a manner that the light-permeable element 98 is detachably mounted thereon. Such construction permits the light-permeable element 98 to be replaced so as to be accommodated to a semiconductor device having bonding sections varied in height. For example, the light-permeable element or glass plate 98 as shown in FIG. 10(a) may be used which is formed on the surface thereof with at least one step 114 to divide the surface into a plurality of sections 116 different in thickness from each other. In FIG. 10(a), the surface of the glass plate 98 is divided into three such sections 116a, 116b and 116c. Alternatively, such a glass plate 98 as shown in FIG. 10(b) may be used which is constructed to have an oblique surface 118 to cause the thickness of the plate 98 to be gradually and continuously varied. In addition to the above, the arm 100 may be constructed to cause its rotation angle and/or length to be varied as desired, so that a portion of the glass plate 98 which has a thickness T accommodated to the difference H may be positioned below the high magnification image pickup unit 96.

Further, a suitable lens may be used as the light-permeable element 98.

The above description has been made with respect to a semiconductor device having two bonding sections. However, it is a matter of course that the high magnification image pickup mechanism may be applicable to a semiconductor device having three or more bonding sections. In this case, a plurality of light-permeable elements may be used. In the glass plate 98 shown in FIG. 10 (a), each of the sections 116a, 116b and 116c may serve as one light-permeable element or glass pate, and the glass plate 98 of FIG. 10(b) may include a plurality of glass plates.

As can be seen from the foregoing, the high magnification image pickup mechanism 46 which may be incorporated in the illustrated embodiment is constructed to include the high magnification image pickup unit 96 and the light-permeable element 98 having a refractive index different from that of air and the light-permeable element 98 is retractably interposed between a semiconductor device to be inspected and the high magnification image pickup unit 96. This results in the focal distance of the optical system of the high magnification image pickup mechanism 46 being easily varied between image pickup carried out by means of only the image pickup unit 96 and that carried out by means of a combination of the image pickup unit 96 and light-permeable element 98. Accordingly, the high magnification image pickup mechanism 46 allows a plurality of sites different in height on a semiconductor device to be readily inspected by only moving the light-permeable element 98 of small size and light weight without requiring any troublesome operation, such as varying the focal distance of the image pickup device, vertically moving the image pickup unit or semiconductor device, or the like. Also, selection of a suitable light-permeable element permits the focal distance of the optical system of the image pickup mechanism to be further varied. Thus, it will be understood that the high magnification image pickup mechanism accomplishes high magnification visual image inspection of a semiconductor device due to pickup of a plane image of a semiconductor device at high speed and with high accuracy.

Further, it should be understood that the high magnification image pickup mechanism constitutes the semiconductor device inspection system of the present invention or a high magnification one by itself.

In the semiconductor device inspection system of the illustrated embodiment, the marking mechanism 54 is adapted to put a failure mark on the IC chip or semiconductor device depending on an inspection signal generated from the low magnification image pickup mechanism 44 or high magnification image pickup mechanism 46 so as to exclude the defective semiconductor device at a subsequent step.

Figure 11:
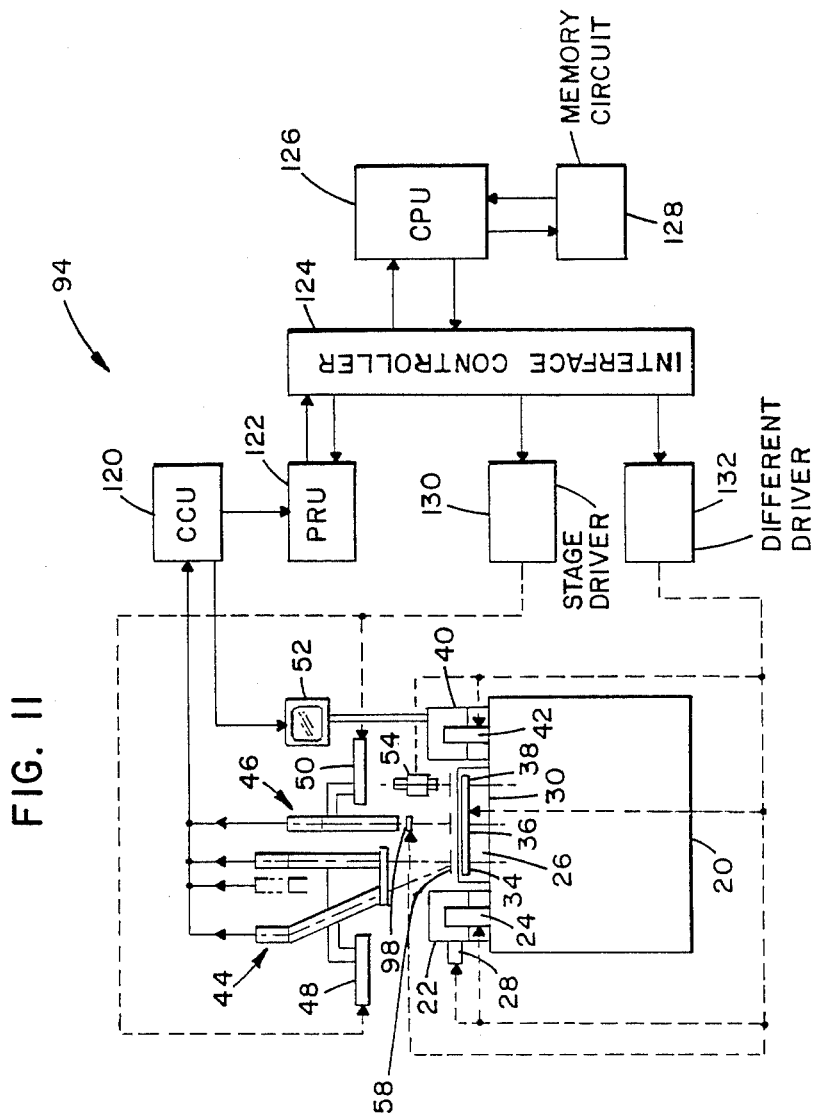
FIG. 11 is a schematic diagram showing a signal processing means.

FIG. 11 shows the signal processing means 94 and a signal processing path in detail, wherein reference numerals 120, 122, 124, 126, 128, 130 and 132 designate a camera control unit (CCU), a pattern recognition unit (PRU) serving as an image processing device, an interface controller, a central processing unit (CPU), a memory circuit, a stage driver and a different driver, respectively, and which same above reference numerals together constitute the signal processing means 94. Signals generated from the image pickup mechanism 44 and 46 are processed by the signal processing means 94 and through the signal processing path shown in FIG. 11, so that a driving section of the inspection system arranged on the left half of FIG. 11 may be actuated as desired.

The memory circuit 128 has an operation program stored therein which is used to synthesize standard data of each inspection item or plane position data obtained by two of the low magnification image pickup units 70 or the high magnification image pickup unit 96 to obtain a three-dimensional position of a bonding section by operation.

The camera control unit 120 is adapted to carry out one frame scanning of a whole visual field or frame scanning of each of a plurality of blocks defined by dividing the visual field to generate a digital image pickup signal. The pattern recognition unit 122 is adapted to compare its input signal which is the digital image pickup signal generated from the camera control unit 120 with a standard data signal based on standard data stored in the memory circuit 128 to judge whether the input signal is normal and then feed it to the marking 54 when it is not normal to cause the mechanism 54 to put a failure mark on a defective IC chip.

The visual monitor device 52 is adapted to display inspection information such as inspected numerical values, failed bonding sections, analysis of a failure in bonding and the like in addition to the image picked up by the image pickup mechanism 44 or 46 at a real time, so that the information may be immediately fed back to a bonding machine (not shown) to take necessary steps, such as varying bonding conditions.

Inspection data obtained by the system of the illustrated embodiment may be totaled so that a rapid and appropriate response may be made to failure in bonding in any previous step, resulting in the manufacturing yields of a semiconductor device being significantly increased.

Figure 12:
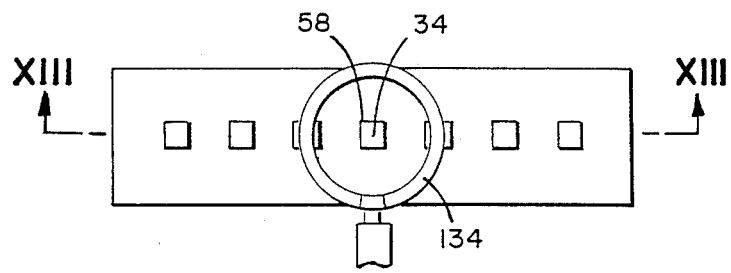
FIG. 12 is a plan view showing a lighting equipment.
Figure 13:
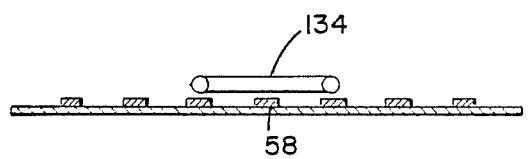
FIG. 13 is a sectional view taken along line XIII—XIII of FIG. 12.

FIGS. 12 and 13 illustrate a lighting equipment 134 used for the low magnification inspection position or point 34, which includes an annular light source and is arranged in a manner to surround an IC chip 58 of a semiconductor device positioned at the low magnification inspection point 34 and be in proximity to an inspected surface of the chip. Such arrangement of the lighting equipment 134 permits the lighting equipment 134 to exhibit illumination sufficient to cause the low magnification image pickup unit 70 to carry out accurate image pickup of a three-dimensional configuration of a bonding wire 124.

As can be seen from the foregoing, the illustrated embodiment is constructed in such a manner that a plurality of the low magnification image pickup units are arranged so as to cause their central axes to intersect together on a surface of a semiconductor device to be inspected. Such construction permits each of the image pickup units to use a lens of a low magnification which is capable of exhibiting a wide visual field and a large focal depth sufficient to prevent distortion of an obtained low magnification image irrespective of oblique image pickup. This facilitates focusing of the low magnification image pickup units on the inspected surface of the semiconductor device without any troublesome operation, such as that of moving them in vertical and/or horizontal directions, resulting in the low magnification image pickup being accomplished with ease and in a short period of time.

Also, the embodiment may include the high magnification image pickup mechanism which includes the high magnification image pickup unit and the light-permeable element having a refractive index different from that of air, wherein the light-permeable element is retractably interposed between a semiconductor device to be inspected and the high magnification image pickup unit. Such construction allows a plurality of sites different in height on a semiconductor device to be readily inspected by only moving the light-permeable element without requiring any troublesome operation, such as varying the focal distance of the image pickup device, vertically moving the image pickup unit or semiconductor device, or the like, so that high magnification visual image inspection of a semiconductor device due to pickup of a plane image of the semiconductor device may be effectively accomplished at high speed and with high accuracy.

Further, in the illustrated embodiment, the data of image pickup is subjected to digital processing for comparison with the standard data, so that the correctness of bonding on a semiconductor device may be judged. Accordingly, many signals of many bonding sections on the whole area of the semiconductor device observed with a wide visual field can be rapidly compared with the standard data, resulting in inspection time being substantially shortened to a degree sufficient to improve inspection efficiency. Further, the correctness of the input data is quantitatively judged to eliminate any variation of inspection caused by an inspector.

Thus, it will be noted that the semiconductor device inspection system of the present invention effectively and readily accomplishes visual image inspection of a semiconductor device in a short period of time with high accuracy.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cove all the generic and specific features of the invention herein described and all statements of the scope of the invention which, as a matter of language, might be said to fall therebetween.

What is claimed is:

1. A semiconductor device inspection system for carrying out visual image inspection of a semiconductor device subjected to wire bonding and supported on a base, comprising:

at least one image pickup mechanism comprising; a plurality of image pickup units each of which carries out image pickup of said semiconductor device to generate an image signal, said image pickup units each including a lens system having at least one lens and a light receptor for receiving thereon an image formed by said lens system;

an optical-electrical signal converter means connected to said image pickup units for converting each of said image signals into an electrical signal;

an operation circuit connected to said optical-electrical signal converter to digitize said electrical signal, said operation circuit digitizing electrical signals derived from at least two of said image pickup units and converted by said converter and synthetically operating the digitized of an inspected section of said semiconductor device;

a memory circuit for storing digitized standard data on an inspection item therein; and an image processing unit connected to said operation circuit to compare an input data signal obtained by digitizing said electrical signal with a standard data signal based on said digitized standard data to judge the normality of said input data signal;

said image pickup units being arranged in a manner such that central axes of said image pickup units each defined by connecting a center of said light receptor and a center of said lens system together intersect one another on said inspected surface of said semiconductor device, consequently, the central axis of at least one image pickup unit is oblique to said inspected surface of said semiconductor device, and that, said light receptor of each of said image pickup units, including said at least one oblique image pickup unit, is arranged in parallel to an inspected surface of said semiconductor device.

2. A semiconductor device inspection system as defined in claim 1, wherein said image pickup mechanism is a low magnification image pickup mechanism.

3. A semiconductor device inspection system as defined in claim 2 further comprising a high magnification image pickup mechanism connected to said optical-electrical signal converter means.

4. A semiconductor device inspection system as defined in claim 3, wherein said high magnification image pickup mechanism comprises a high magnification image pickup unit and a light-permeable element having a refractive index different from that of air;

said light-permeable element being arranged in a manner to be retractably interposed between said high magnification image pickup unit and said semiconductor device.

5. A semiconductor device inspection system as defined in claim 1, wherein said lens system is arranged in a manner such that a lens plane thereof perpendicular to a lens axis is parallel to said inspected surface of said semiconductor device.

6. A semiconductor device inspection system for carrying out visual image inspection of a semiconductor device subjected to wire bonding and supported on a base, comprising:

a loading mechanism for receiving therein a semiconductor device on which wire bonding has been completed;

a transfer mechanism for transferring the semiconductor device fed from said loading mechanism through an inspection stage;

an unloading mechanism for receiving the semiconductor device discharged from said transfer mechanism;

an image pickup means for carrying out image pickup of an inspected surface of the semiconductor device on said inspection stage to generate and image signal wherein said image pickup means comprises a low magnification image pickup mechanism and a high magnification image pickup mechanism and said image pickup means is oblique to said inspected surface of said semiconductor device;

a memory circuit for storing standard data therein;

an image processing unit connected between said image pickup means and said memory circuit to carry out digital processing of said image signal and compare said digitized image signal with said standard data stored in said memory circuit to judge the correctness of said wire bonding and generate a judgment signal; and a marking mechanism of carrying out marketing indicative of the correctness of the semiconductor device depending on said judgment signal from said image processing unit.

7. A semiconductor device inspection system as defined in claim 6, wherein said low magnification image pickup mechanism has a visual field which covers an IC chip and a whole circumference thereof and said high magnification image pickup mechanism has a visual field which covers a pad or lead and a circumference thereof.

8. A semiconductor device inspection system comprising:

a base for holding a semiconductor device thereon; and an image pickup mechanism for carrying out plane image pickup of said semiconductor device to inspect a visual image of said semiconductor device;

said image pickup mechanism comprising an image pickup unit and a light-permeable element having a refractive index different from that of air;

said light-permeable element being arranged in a manner to be retractably interposed between said image pickup unit and said semiconductor device.

9. A semiconductor device inspection system as defined in claim 8, wherein said image pickup unit generates a signal indicating the result of said image pickup.

10. A semiconductor device inspection system as defined in claim 10 further comprising a signal processing means connected to said image pickup mechanism to process said signal for inspection.

11. A semiconductor device inspection system as defined in claim 8, wherein said light-permeable element comprises a flat glass plate.

12. A semiconductor device inspection system as defined in claim 11, wherein said glass plate has surfaces parallel to each other.

13. A semiconductor device inspection system as defined in claim 12, wherein said glass plate is provided on one of said surfaces with at least one step so that it may be divided into a plurality of sections different in thickness from each other.

14. A semiconductor device inspection system as defined in claim 12, wherein one of said surfaces of said glass plate is inclined to cause the thickness of said glass plate to be gradually and continuously varied.

15. A semiconductor device inspection system as defined in claim 8, wherein said image pickup mechanism is arranged so as to be horizontally moved in X and Y directions.

16. A semiconductor device inspection system as defined in claim 15, wherein said light-permeable element is supported on said image pickup unit.

17. A semiconductor device inspection system as defined in claim 16, wherein said light-permeable element is supported on said image pickup unit through a holder which is mounted on said image pickup mechanism, to thereby be pivotally moved about a vertical axis.

18. A semiconductor device inspection system comprising:

a base for holding a semiconductor device thereon;

an image pickup mechanism for carrying out plane image pickup of said semiconductor device to generate a signal indicating the result of said plane image pickup, said image pickup mechanism being arranged so as to be horizontally moved in X and Y directions; and a signal processing means connected to said image pickup mechanism to process said signal generated from said image pickup mechanism for inspection;

said image pickup mechanism comprising an image pickup unit and a light-permeable element supported on said image pickup unit and having a refractive index different from that of air;

said light-permeable element being arranged in a manner such that it is pivotally moved about a vertical axis so as to be retractably positioned between said image pickup unit and said semiconductor device.

* * * * *